(12) United States Patent
Moore (10) Patent No.: US 8,053,745 B2
(45) Date of Patent: Nov. 8, 2011

(54) DEVICE AND METHOD FOR ADMINISTERING PARTICLE BEAM THERAPY

(76) Inventor: John F. Moore, Libertyville, IL (US)

( * ) Notice: Subject to any disclaimer, the term of this patent is extended or adjusted under 35 U.S.C. 154(b) by 318 days.

(21) Appl. No.: 12/391,831

(22) Filed: Feb. 24, 2009

(65) Prior Publication Data

US 2010/0213385 A1    Aug. 26, 2010

(51) Int. Cl.
*A61N 5/10* (2006.01)
*G21K 5/10* (2006.01)
(52) U.S. Cl. ........... 250/492.1; 250/492.3; 600/1; 600/2
(58) Field of Classification Search .............. 250/396 R, 250/397, 492.1, 492.3; 600/1, 2
See application file for complete search history.

(56) References Cited

U.S. PATENT DOCUMENTS

| | | |
|---|---|---|
| 3,257,556 A | 6/1966 | Boetcker et al. |
| 3,986,026 A | 10/1976 | Martin |
| 5,117,829 A | 6/1992 | Miller et al. |
| 5,760,395 A | 6/1998 | Johnstone |
| 5,847,401 A | 12/1998 | McKeown et al. |
| 5,895,926 A | 4/1999 | Britton et al. |
| 6,087,670 A | 7/2000 | Hiramoto et al. |
| 6,275,564 B1 | 8/2001 | Ein-Gal |
| 6,639,234 B1 | 10/2003 | Badura et al. |
| 6,683,318 B1 | 1/2004 | Haberer et al. |
| 6,730,921 B2 | 5/2004 | Kraft |
| 6,809,325 B2 | 10/2004 | Dahl et al. |
| 6,814,694 B1 | 11/2004 | Pedroni |
| 7,084,410 B2 | 8/2006 | Beloussov et al. |
| 7,154,108 B2 | 12/2006 | Tadokoro et al. |
| 7,247,869 B2 | 7/2007 | Tadokoro et al. |
| 7,268,358 B2 | 9/2007 | Ma et al. |
| 7,280,633 B2 | 10/2007 | Cheng et al. |
| 7,317,192 B2 | 1/2008 | Ma |
| 7,345,292 B2 | 3/2008 | Moriyama et al. |
| 7,368,740 B2 | 5/2008 | Beloussov et al. |
| 2006/0050847 A1 | 3/2006 | Jaffray et al. |
| 2006/0159220 A1* | 7/2006 | Heuscher .......................... 378/9 |
| 2007/0034812 A1 | 2/2007 | Ma et al. |
| 2007/0176125 A1 | 8/2007 | Natori et al. |
| 2008/0009717 A1* | 1/2008 | Herrmann et al. ............ 600/425 |
| 2008/0093567 A1 | 4/2008 | Gall |
| 2008/0137805 A1 | 6/2008 | Forster et al. |
| 2008/0161676 A1 | 7/2008 | Satragno et al. |
| 2008/0234531 A1* | 9/2008 | Welch et al. ...................... 600/2 |
| 2008/0317216 A1 | 12/2008 | Lifshitz et al. |
| 2009/0202045 A1* | 8/2009 | Guertin et al. ................. 378/195 |
| 2010/0329422 A1* | 12/2010 | Brown et al. .................... 378/65 |

* cited by examiner

*Primary Examiner* — Robert Kim
*Assistant Examiner* — Nicole Ippolito Rausch
(74) *Attorney, Agent, or Firm* — Drinker Biddle & Reath LLP (57) ABSTRACT

A device for circumscribing a target site with a beam. The target site is located within a target body. The path of the beam is varied rotationally so as to form a cone with an isocenter at the cone's apex. The isocenter is fixed on the approximate center of the target site. The target body is rotated about a vertical axis passing approximately through the center of the target site, and the rates of rotation of the beam path and body, respectively correspond so that the beam intersects an axis passing through the target site at an approximately constant angle.

16 Claims, 7 Drawing Sheets

DEVICE AND METHOD FOR ADMINISTERING PARTICLE BEAM THERAPY

BACKGROUND OF THE INVENTION

It is known to use directed beams of particles, including but not limited to protons, heavier ions (such as carbon), and mesons, to attack and destroy cancer cells. Particle therapy has an advantage over traditional radiation therapy in that the particle beam can be directed to a particular depth within a patient's body; because, unlike an x-ray beam, the particle beam deposits little energy in the tissue through which it passes, but deposits a large amount of energy at its end point, the beam can kill cancer cells with minimal damage to intervening tissue. Dose to the tissue surrounding the tumor is further reduced by arranging for the beam to reach the tumor from many different directions, such as over an arc of up to 360 degrees. Conventional particle therapy involves generating a beam of fast-moving particles in a particle accelerator or a cyclotron. The beam is then directed along a desired path toward a patient. Because the beam must be delivered to the entire circumference of the target site, current systems direct the beam at the patient from a gantry rotating around the patient.

Conventional particle therapy devices place the patient in a horizontal position, and use magnets arranged in large gantry assemblies to direct the beam at the patient from locations around a 360-degree circumference. Because of the size of the particle beam generator, the magnets required to deflect the beam by a total of close to 180 degrees, and the gantry, this arrangement requires deep excavation at huge cost. Current systems incorporate gantries four or more meters in diameter, weighing over 90 tons. Further, the varying direction of the beam mandates that extensive radiation shielding is required around the entire circumference of the treatment area.

There is, therefore, a need for a particle therapy device and method that requires a smaller and less complicated structure.

DETAILED DESCRIPTION OF THE EMBODIMENTS

Figure 1:
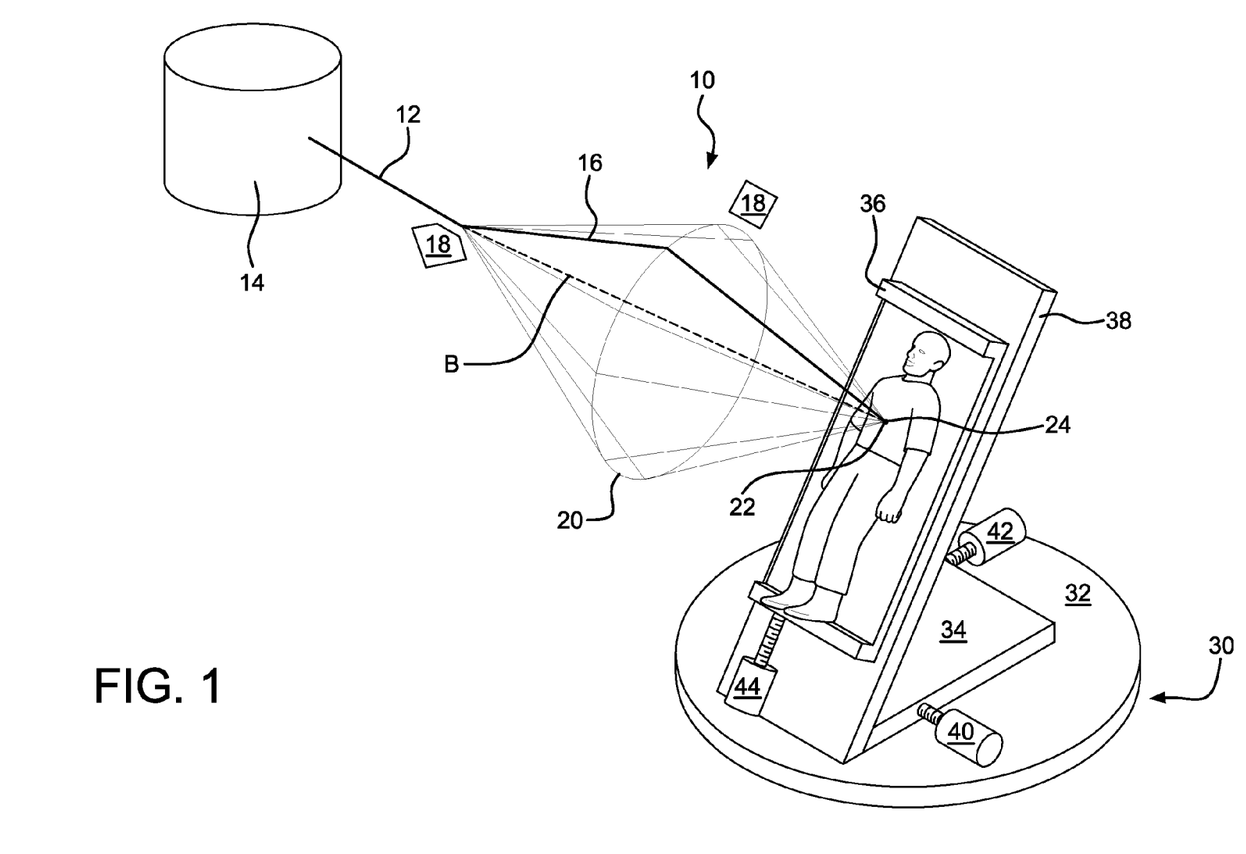
FIG. 1 is an isometric view of an embodiment of the system of the present invention, showing the rotation of the beam through a treatment cycle but not showing rotation of the patient.
Figure 4A:
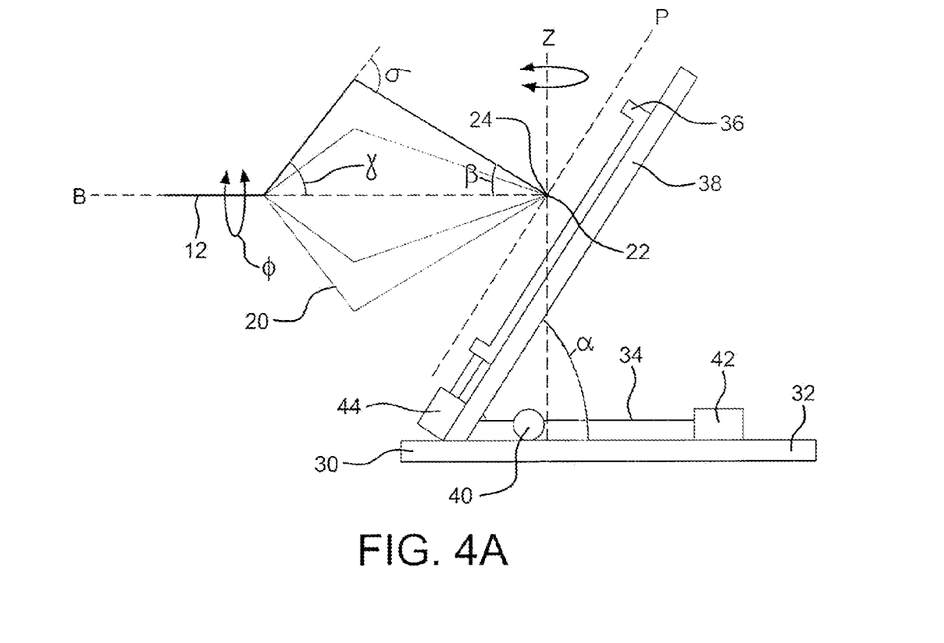
FIG. 4A is a side view of an embodiment of the system of FIG. 1, showing the patient table in relation to the beam, and showing the motion of the beam through the treatment cycle, but not showing rotation of the table.

FIG. 1 shows a representation of an embodiment of the system 10 of the present invention. A beam 12 is generated by a beam generator 14, which may be a cyclotron or similar device. While the beam may be any type of beam, including optical and particle beams, "beam" or "particle beam" as used herein is intended to describe any suitable type of beam. The beam is directed along a path 16 by path guides 18, which are preferably magnets for a particle beam, but which may be any device suitable for deflecting the path of a given type of beam. As shown in FIGS. 2A-2D, the path 16 is bent at a first angle $\gamma$ and a second angle $\sigma$. While the first angle $\gamma$ and the second angle $\sigma$ remain constant for a particular treatment cycle, the beam path varies in a rotation around axis B, which is coaxial with the path of the beam 12 prior to deflection at the first angle $\gamma$, as shown in FIGS. 1 and 4A. The angles $\gamma$ and $\sigma$ can be any angles that provide the desired system geometry. The rotation of the beam path forms a cone 20 with a fixed isocenter 22 at its apex and located along the axis B. The rotation may occur in either the clockwise or counterclockwise direction. While the beam path varies, the beam continually passes through the isocenter, which is positioned at a target site 24 located within or on a body 26, including but not limited to the site of a tumor inside the patient's body. While the system may be used to direct a beam of any type to a target site on a body generally, the system will be generally described herein in the context of the treatment of a tumor in a human patient.

As the beam path 16 rotates around the axis B (as shown in FIG. 1), the patient assembly 30 simultaneously rotates around a vertical axis Z, as seen in FIGS. 2A, 2B, 4A, and 4B. The assembly 30 includes a rotating platform 32 and a patient cradle 34. The cradle includes a patient tray 36 mounted to a frame 38. The frame and tray are movable in multiple degrees of freedom, and may be moved by motors 40-46 positioned to adjust the position of the tray in any number of desired directions, in order that the target within the patient remains at the isocenter 22 during rotation of the patient assembly 30. In the embodiment shown in FIGS. 4A and 4B, motor 40 moves the frame 38 in a direction X; motor 42 moves the frame 38 in a direction Y perpendicular to direction X, and motor 44 moves the tray 36 in along axis P. Motor 46 allows the angle $\alpha$, shown in FIG. 3B, to be adjusted if needed; e.g., to compensate for deflection of the patient cradle or tray, or to adjust the angle at which the beam enters the patient's body. These degrees of freedom allow the patient to be positioned so that the platform's axis of rotation Z passes through the tumor located at target site 24.

Figure 6:
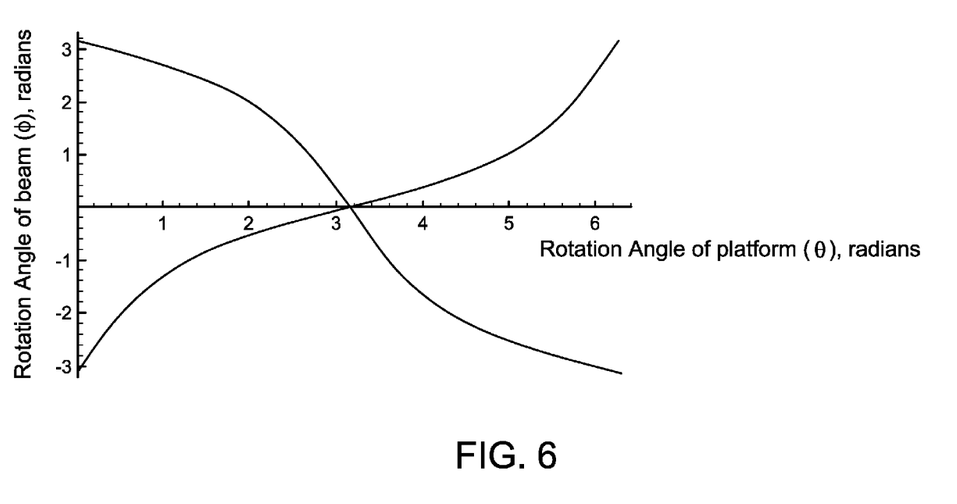
FIG. 6 is a graph showing the respective angles of rotation of the beam and the platform, in which each function line shows a different direction of rotation.

The rotation of the assembly 30 about axis Z may be in either the clockwise or counterclockwise direction, and corresponds with the rotation of the beam path 16 about axis B. As shown in FIGS. 2A-2D, the respective rotations are synchronized so that the beam 12 always contacts the patient 26 at roughly a right angle to the patient's body without the use of an large-diameter gantry structure, as is the case for a horizontal patient. As will be understood by one of ordinary skill in the art, the respective rates of rotation of the assembly and beam path need not be constant. Similarly, one of ordinary skill will appreciate that the relationship between the rates of rotation of the assembly and the beam, respectively, need not be linear. One embodiment of the relationship between the rates of rotation is shown in FIG. 6, wherein each function line depicts a different direction of rotation of the beam path.

Figure 2A:
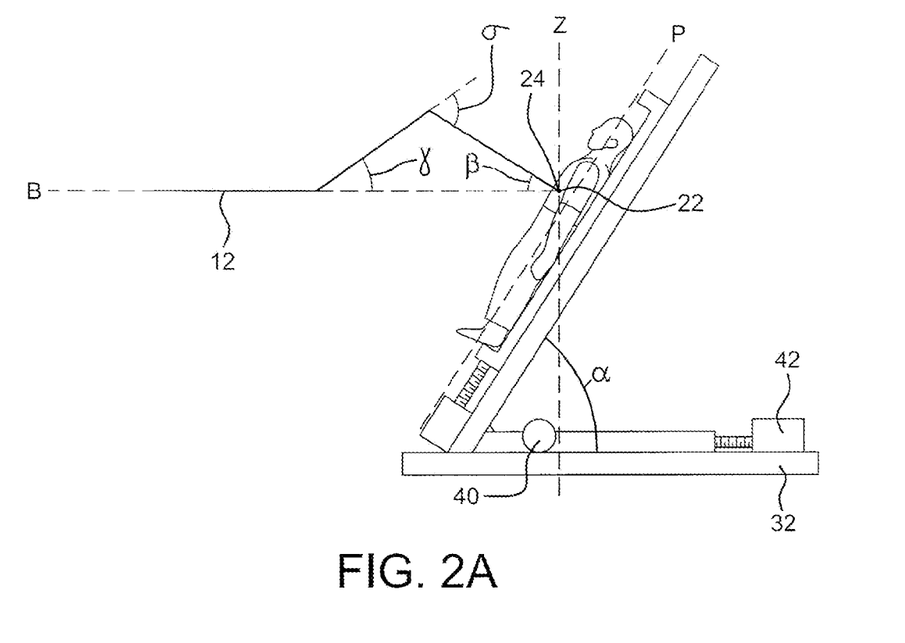
FIG. 2A is a side view of an embodiment of the system of FIG. 1, showing the position of the beam and the patient at one point in a treatment cycle.
Figure 2B:
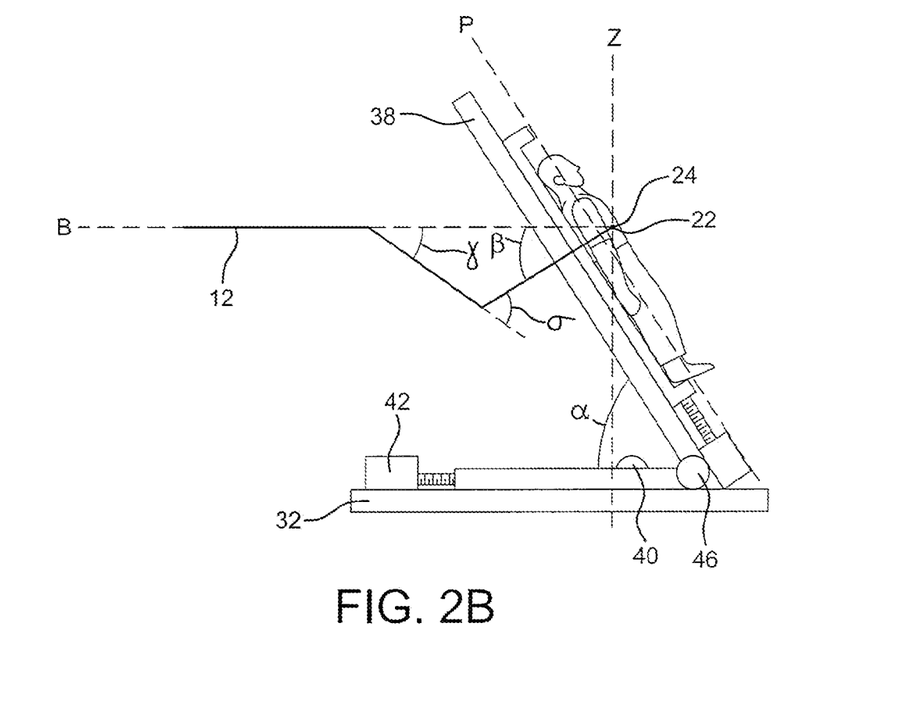
FIG. 2B is a second side view of an embodiment of the system of FIG. 1, showing the position of the beam and the patient at a second point in the cycle.
Figure 2C:
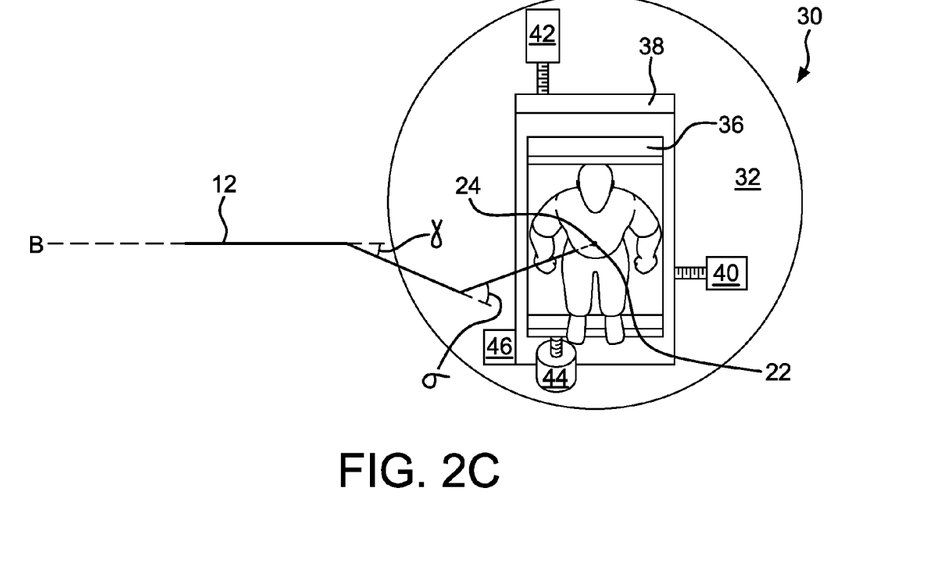
FIG. 2C is a top view of an embodiment of the system of FIG. 1, showing the position of the beam and the patient at a third point in the cycle.
Figure 2D:
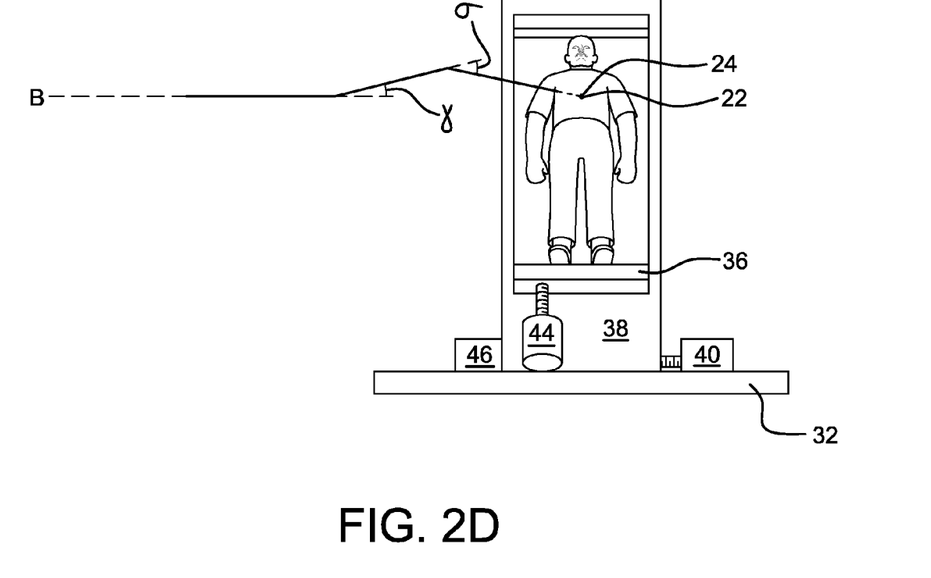
FIG. 2D is a front view of the position of the beam and the patient at the point in the cycle shown in FIG. 2C.

FIGS. 2A-2D show how the beam 12 contacts the patient's body at various times during a treatment cycle. FIG. 2A is a side view of the arrangement at a first point in the cycle. The patient is located on the tray 36 of the assembly 30. The beam 12 is directed through first and second angles γ and σ, respectively, and contacts the tumor located at target site 24. As will be described, the position of the patient may be varied in order to maintain the target site in a constant location in space, and to maintain beam contact with the site throughout the treatment cycle. FIG. 2B is a side view of a second point in the cycle. As shown in FIGS. 2A and 2B, the beam contacts the target site 24 at approximately 90 degrees from the axis P. FIG. 2C is a view of a third point in the treatment cycle, as seen from the same location in space as FIGS. 2A and 2B. The assembly 30 has rotated 90 degrees around axis Z, which runs through roughly the center of the tumor located at the target site 24. Because the assembly preferably rotates around an axis passing through the center of the target site, the target site's spatial orientation preferably remains constant; i.e., the site does not move laterally, but rather merely rotates in place. As seen in FIGS. 2A-2C, the rates of rotation are synchronized in a non-linear fashion, so that the beam is still contacting the target site at an angle of roughly 90 degrees from the axis P. As seen in FIG. 2B, the assembly 30 has rotated 180 degrees from its orientation shown in FIG. 2A. The beam 12 has also rotated a corresponding amount, and still contacts the target site 24 at approximately 90 degrees from the axis P. As seen in FIGS. 2A-2D, the beam isocenter 22 remains aligned with the target site 24 throughout the treatment cycle.

Figure 3A:
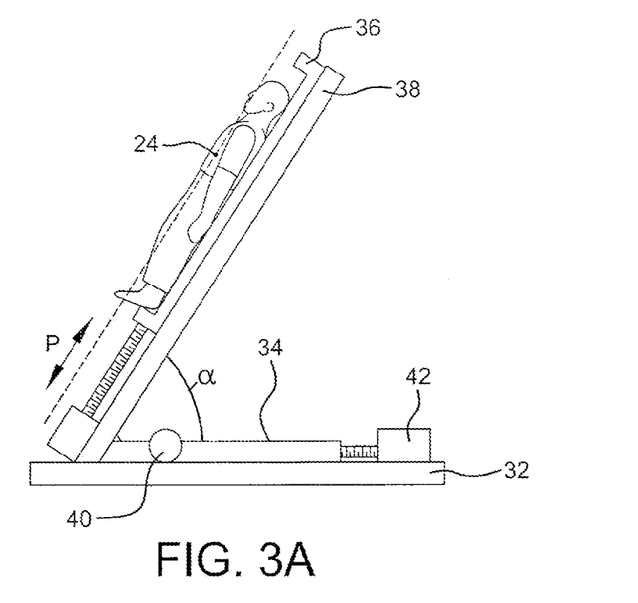
FIG. 3A is a side view of an embodiment of the system of FIG. 1, showing the patient in a first treatment position.
Figure 3B:
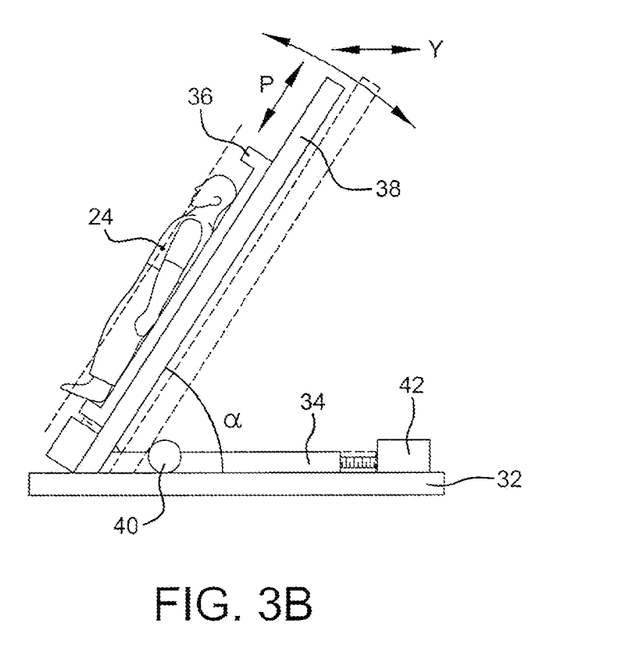
FIG. 3B is a side view of an embodiment of the system of FIG. 1, showing the patient in a second treatment position.
Figure 4B:
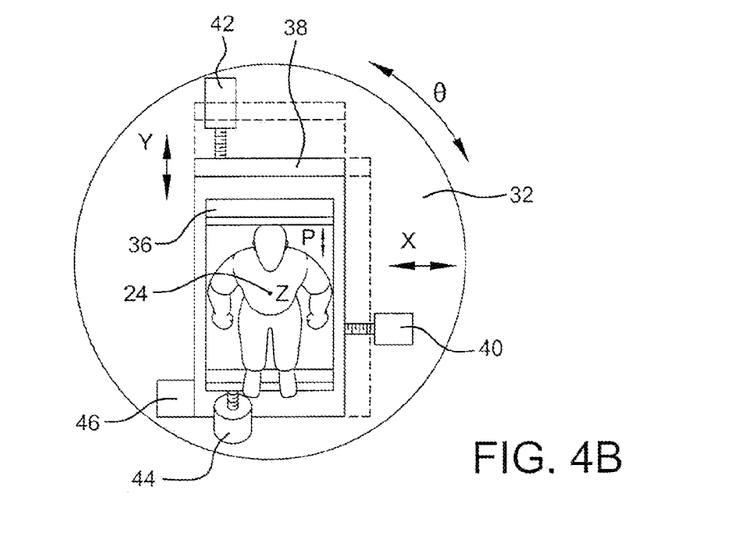
FIG. 4B is a top view of an embodiment of the patient table of FIG. 4A.

In order to properly position the patient for treatment and ensure that the beam isocenter remains fixed on the target site, the assembly 30 should be highly adjustable. As seen in FIGS. 3A, 3B, and 4B, the cradle 34, frame 38, and tray 36 may all be adjusted for position. The assembly 30 includes a platform 32, which rotates around an axis Z passing vertically through the target site's approximate center. In order to accomplish this, the frame 38 can be adjusted in directions X and Y, and the tray 36 can be adjusted along axis P to compensate for location of the target site within the body.

Figure 5:
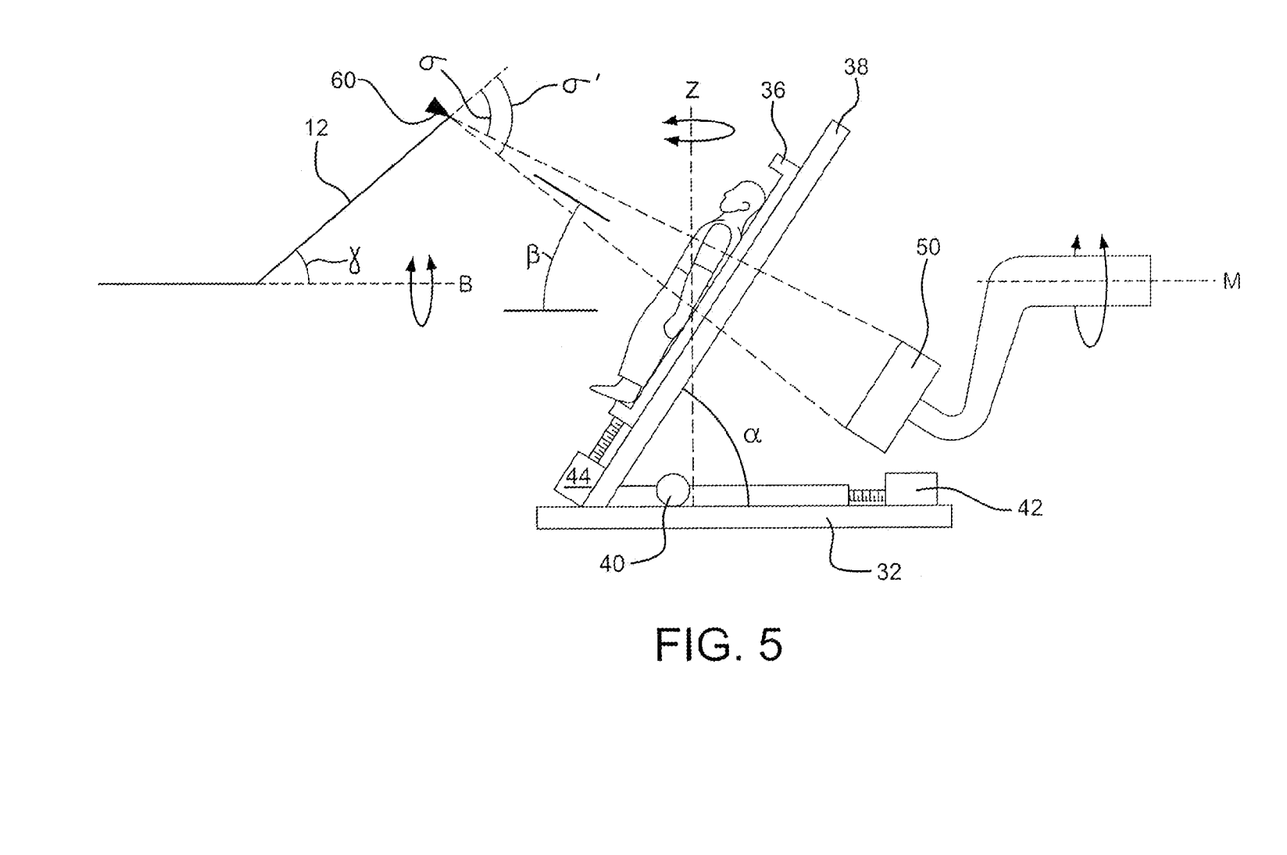
FIG. 5 is a side view of another embodiment of the system of the present invention.

Depending on the rotational mechanism used, the rotating platform 32 preferably rotates about its own center axis. The motor 40 is used to position the frame 38 in the X direction. The motor 42 is used to position the frame in the Y-direction. The motor 44 is used to position the tray 36 along the axis P, and the motor 46 is used to set the angle α of the tray. The tray may be set at any desired angle α at which the patient is comfortable, but the angle α is preferably maintained at an angle corresponding to the chosen γ and σ angles so that the beam enters the patient's body at the desired angle. While the beam preferably enters the patient's body at a roughly 90-degree angle, any suitable angle may be chosen to minimize potential damage to healthy intermediate tissue. The angle α will generally be set between approximately 30 and 60 degrees, as shown in FIG. 5. The adjustability of angle α may also be used to compensate for deflection of the cradle 34 or frame 38 under a range of patient sizes or weights. The frame is sturdy enough to support the weight of the patient, and may be made of any suitable material, including metal or plastic. While the frame is depicted as being supported at its lower edge, it and the cradle 34 may be any shape or material that does not interfere with the beam path 16.

If the target site cannot be positioned along the assembly's axis of rotation, the beam path may be adjusted to ensure full coverage of the target site. As will be understood by those of ordinary skill in the art, the path followed by the particles or other particles may be varied in either or both of two ways for the purpose of accurately covering the full volume of an extended tumor, whose center may lie at the nominal isocenter of the beam. One variation is to introduce a computer-controlled variable-thickness "wedge", whose effect will be to alter slightly the depth at which the beam deposits its energy, thus reaching from the near side to the far side of the tumor at each angle by which it is irradiated. The other variation is to apply an additional small magnetic field or other deflecting method, so as to move the beam slightly from side to side or in a raster pattern, thus covering the (possibly irregular) width of the tumor. These adjustments can occur sufficiently rapidly to perform a three-dimensional scan of the entire tumor volume at each angle of the radiation.

FIG. 5 shows an alternative embodiment of the invention, in which the invention is used to perform a scan, such as a CT scan, of a patient's body. In this embodiment, the beam can be any type of beam necessary to perform the scan. A detecting device 50 can be included in the apparatus. If a 360 degree scan is needed, the detecting device 50 can rotate about an axis M so as to maintain alignment with the beam 12, which may be a thin "pencil" beam, or a beam that forms a cone shape as shown in FIG. 5. The beam may be a particle beam, or it may be another type of beam, such as an x-ray beam generated by a device included along the path of the particle beam. The detector may be any type that is suitable for detecting the beam generated. It is preferred that the beam and patient rotate in a manner identical to that expected to be used during therapy; however, the patient may or may not rotate, depending on the type of image desired. Additionally, if the scan is a linear scan, i.e., along a length of the patient's body, the assembly may remain stationary, and the frame or tray may be moved to ensure proper coverage by the beam of the area to be scanned. Alternatively, any or all of the angles γ, σ, or β may be varied to change the location in which the beam contacts the patient's body, and the detector may move in a corresponding manner. Similarly, the scan may be performed using the same method or device on any object requiring a 3-D scan.

FIG. 6 shows a graphical representation of the relation between the conical rotation of the beam about its horizontal axis and the rotation of the patient about its vertical axis, as required to have the beam traverse the exact circumference of the body. Optionally, intentional, controlled variation from the angles depicted in FIG. 6 can widen the points of entry to a belt of varying width, further reducing the dose to the intervening tissue, while still being focused on the target tumor. For example, in the position of FIG. 2A, where the patient is facing toward the beam and is tilted backward (defined as θ=±180° or ±π radians), the beam is in a topmost position (defined as φ=0° or 0 radians). The beam intersects the patient body at the front. In the position of FIG. 2B, where the patient is facing away from the beam (defined as θ=0° or 360°, or 0 or 2π radians), the beam is in its lowest position (defined as φ=±180° or ±2π radians). The beam intersects the patient body at the back. The intermediate cases are less simple, as two positions of the beam are possible. To clarify this, consider a small counterclockwise rotation (as seen from above) of the patient from the position in FIG. 2A toward the viewer. There are then two points on the circumference of the body that intersect the cone 20, one corresponding to a point closer to the viewer, and the other to a point away from the viewer. The former entails a counter-clockwise rotation of the beam around the cone (as seen from the patient), and the other entails a clockwise rotation. For example, if the patient is facing at right angles to the beam, as in FIGS. 2C and 2D, with the patient angle θ=90° or π/2 radians, the beam must be somewhat above or somewhat below the horizontal. In summary, the relationship between the two angles is non-linear in the manner shown in FIG. 6. Either of the curved paths may be followed, as long as the one chosen is consistent for the full 360° or 2π radians of rotation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A device for circumscribing a three-dimensional target site with a beam, comprising:
   a beam generation device;
   a device arranged to direct the beam along a path in a plane, wherein a beam path from the device rotates about a horizontal axis so that the beam describes a cone of fixed opening angle with an isocenter at the apex of the cone, and wherein the isocenter remains fixed relative to a target site;
   a holding apparatus adapted to secure a body having the target site contained therein, wherein the body is oriented longitudinally along a body axis extending at an angle between horizontal and vertical, such that the sum of the angle of the body axis above the horizontal and an angle between an axis of the cone and any line in the cone substantially equals a right angle, and wherein the apparatus rotates the body about a vertical axis passing approximately through the center of the target site, simultaneously with the rotation of the beam path.

2. The device of claim 1, wherein the beam is a particle beam.

3. The device of claim 1, wherein the path includes magnets as guides for the beam.

4. The device of claim 1, wherein the beam generation device is a cyclotron.

5. The device of claim 1, wherein the path includes at least two angles.

6. The device of claim 1, wherein the beam rotation around the axis of the cone has a controlled relationship with the rotation of the apparatus so that the beam contacts the target site around a circumference of the body at approximately a right angle to the body axis during a 360° rotation of both the beam and the holding apparatus.

7. The device of claim 1, wherein the holding apparatus further comprises:
   a rotatable platform;
   a frame mounted to the platform; and
   a tray adapted to secure the body.

8. The device of claim 7, wherein the frame is movably mounted to the platform.

9. The device of claim 7, wherein the tray is movably mounted to the frame.

10. The device of claim 1, wherein the beam rotation corresponds with the rotation of the apparatus so that the beam contacts the target site at an angle other than a right angle to the body axis.

11. A method of circumscribing a three-dimensional target site with a beam, comprising:
    generating a beam;
    directing the beam along a path so that the beam passes through a predetermined point, wherein the path includes at least a first angle and a second angle;
    rotating the path around an axis so that a portion of the beam emerging from the last of said angles describes a cone with the predetermined point at its isocenter;
    positioning a body so that a target area is located at the isocenter, wherein the body is oriented along an axis having an angle between 30 and 60 degrees from horizontal, the sum of said angle and an angle between the axis of the cone and any line in the cone is substantially a right angle;
    rotating the body about a vertical axis, simultaneously with the rotation of the beam path, so that the target area remains stationary in space; and
    coordinating the two rates of rotation so that the beam contacts the target area in a plane lying at approximately a right angle to the body axis.

12. A device for administering particle beam therapy to a patient, comprising:
    a particle beam generation device;
    a plurality of magnets arranged to direct the beam along a path fixed in a plane that may be rotated so that a beam path from the device describes a cone with an isocenter at the apex of the cone, and wherein the isocenter nominally remains fixed relative to a tumor site; and
    a holding apparatus adapted to secure the patient at an angle above the horizontal such that the sum of said angle and an angle between the axis of the cone and any line in the cone is substantially a right angle, and wherein the apparatus rotates the patient, simultaneously with the rotation of the beam path, about a vertical axis passing approximately through the center of the tumor site, wherein the apparatus includes:
    a rotatable platform;
    a frame movably mounted to the platform;
    a support movably mounted to the frame and adapted to secure the body; and
    wherein the rate of rotation of the beam corresponds to the rate of rotation of the apparatus so that the beam intersects the target site at approximately a right angle to an axis extending along the length of the patient's body and through the approximate center of the tumor site, the axis aligned so that the beam travels the shortest possible path from the surface of the patient's body to the center of the tumor site.

13. The device of claim 12, wherein the patient is oriented at an angle between approximately 30 and 60 degrees from horizontal.

14. A device for conducting a scan of a body, comprising:
a beam generation device;
a device arranged to direct the beam along a path fixed in a plane, wherein the plane rotates about a horizontal axis so as to form a cone with the isocenter at the apex of the cone, and wherein the isocenter remains fixed relative to a target site;
a holding apparatus adapted to secure a body having the target site contained therein, wherein the body is oriented at an angle above the horizontal such that the sum of said angle and an angle between the axis of the cone and any line in the cone is substantially a right angle, and wherein the apparatus rotates the body about a vertical axis passing approximately through the center of the target site, simultaneously with the rotation of the beam path;
an area detector on the opposite side of the body, rotating around an axis co-linear with the axis of rotation of the beam, wherein the rotation of the detector is coordinated with the rotation of the beam so that the detector intercepts the beam after the beam has passed through the target site.

15. The device of claim 14, further comprising an x-ray source located along the path so as to create a three-dimensional image.

16. A method of creating a three-dimensional image, the method comprising:
generating a beam whose path rotates in the shape of a cone;
positioning a body having a target area so that the apes of the cone is located within the target area and wherein the body is oriented along a body axis having an angle from horizontal such that the sum of said angle and an angle between the axis of the cone and any line in the cone is substantially a right angle
rotating the body about a vertical axis passing through the target area so that the target area remains substantially stationary in space;
rotating the beam source about an axis, simultaneously with the rotation of the body;
an area detector oriented normal to the beam and mounted on an axis collinear with that of the cone so as to detect the beam, wherein the target site is located between the beam source and the detector;
coordinating the rates of rotation of the beam, the body, and the detector so that the path from the beam to the detector passes through the target area in a plane lying about the body axis; and
detecting the beam with the detector.

* * * * *